United States Patent [19]
Lorr

[11] Patent Number: 5,112,745
[45] Date of Patent: May 12, 1992

[54] RAPID IDENTIFICATION OF MICROBIAL ORGANISMS AND DETERMINATION OF ANTIBIOTIC SENSITIVITY BY INFRARED SPECTROSCOPY

[75] Inventor: David Lorr, Garrett Park, Md.

[73] Assignee: Space Medical Systems, Inc., Garrett Park, Md.

[21] Appl. No.: 539,599

[22] Filed: Jun. 18, 1990

Related U.S. Application Data

[63] Continuation-in-part of Ser. No. 414,291, Sep. 29, 1989, abandoned.

[51] Int. Cl.⁵ .......................... C12Q 1/02; C12Q 1/18; C12Q 1/04
[52] U.S. Cl. ........................................ 435/38; 435/29; 435/32; 435/34
[58] Field of Search .................. 356/442, 201; 435/29, 435/34, 38, 32; 250/339

[56] References Cited

U.S. PATENT DOCUMENTS

| | | | |
|---|---|---|---|
| 4,017,192 | 4/1977 | Rosenthal | 356/201 |
| 4,384,206 | 5/1983 | Bjarno | 250/339 |
| 4,725,148 | 2/1988 | Endo et al. | 356/442 |
| 4,758,509 | 7/1988 | Ottley | 435/29 |
| 4,847,198 | 7/1989 | Nelson et al. | 435/34 |

OTHER PUBLICATIONS

Solomons (1980) Organic Chemistry Wiley Co N.Y. pp. 558-574.

Primary Examiner—Christine Nucker
Assistant Examiner—David R. Preston
Attorney, Agent, or Firm—Browdy and Neimark

[57] ABSTRACT

A rapid and effective method is provided for determining various genotypic and/or phenotypic characteristics of an unknown microbial organism in a non-destructive manner. Initially, a predetermined growth medium is inoculated with an unknown microbial organism to create a microbial culture and the culture is then scanned at a time after inoculation to obtain a spectral signature. This scanning step is conducted utilizing wavelengths over a portion of the electromagnetic spectrum from 700-5000 nm. Thereafter, characterizing data of the unknown organism is determined from the spectral signature. This characterizing data of the unknown organism is compared with a preexisting library of characterizing data of known organisms with known characteristics, which library was made by scanning known organisms in the same manner as the unknown organism, to determine if there is a match between the characterizing data of the unknown organism and the characterizing data of a known organism contained in the library. When the characteristic of the unknown organism is matched, the identity of the unknown organism has been found. The present method is advantageous in that identity, quantity, growth rate and antibiotic sensitivity of an unknown microorganism can be easily and reliably determined more quickly than would be possible using previously known methods.

29 Claims, 15 Drawing Sheets

RAPID IDENTIFICATION OF MICROBIAL ORGANISMS AND DETERMINATION OF ANTIBIOTIC SENSITIVITY BY INFRARED SPECTROSCOPY

This is a continuation-in-part of Ser. No. 07/414,291, filed Sep. 29, 1989.

FIELD OF THE INVENTION

The present invention relates generally to the rapid identification of microbial organisms, the determination of their characterizing traits (such as antibiotic sensitivities), the determination of their growth rates, and the determination of quantities by near-infrared/Mid-infrared spectroscopy (700–5000 nm). The information is obtained by scanning a sample containing the unknown organism at any point after inoculation, scanning at a preselected time after inoculation, or scanning at a series of preselected time intervals after inoculation. Thereafter the characterizing data obtained from the spectral signatures recorded during the scans are compared with those of previously scanned known organisms until a match is found. It is this matching of characterizing data from the spectral signatures of unknown organisms with the characterizing data of known organisms which have been correlated to genotypic and phenotypic traits that allows inferences to be made about the organism in question.

BACKGROUND OF THE INVENTION

At present most microbial analysis involves three major steps: primary growth and isolation of an organism from a patient source, biochemical diagnostic tests to make a positive identification, and exposure to antibiotic compounds from which the sensitivities of an organism are determined. Each of the major steps requires a twenty-four hour period to execute. Even though the biochemical identification and antibiotic sensitivities can be run concurrently, the total time required to identify an organism and determine the antibiotic of choice for treatment is usually at least forty-eight hours. Besides the time requirements for setting up the procedures and reading the results, current identification procedures are very labor intensive and often require considerable training and experience on the part of laboratory technicians.

In U.S. Pat. No. 4,576,916 (Lowke et al), a method and apparatus for identifying bacteria using electro-optical investigation is disclosed. In particular, a specified quantity of fluid sample believed to contain a given microbial cell is combined with a portion of a fluid sample with an inhibiting reagent having a known effect on the electrical polarizability of the microbial cell. The resulting fluid sample is then placed in an alternating current electric field to cause the alignment of any microbial cells present. When a polarized beam of laser light is passed through the sample, the extent of birefringence is measured and compared with a reference measurement made with a control.

In U.S. Pat. No. 4,758,509 (Ottley), a method of detection of microbial growth is provided. In this method, a culture of an organism is prepared and a portion is taken for analysis in a pyrolysis mass spectrometer. By monitoring the relative height of the peak in the mass spectrum corresponding to a mass of 60 daltons, an increased height of this peak relative to the remainder of the spectrum indicates growth of the microorganism. A second measurement can also be made corresponding to an abundance of ions at one or more masses. This patent also briefly mentions another method whereby a measurement of optical density is made to detect growth. However, it is indicated that this method is only usable where the culture medium is itself reasonably transparent.

In U.S. Pat. No. 4,384,206 (Bjarno), a process for the detection of particular quality properties in articles of food is disclosed. In particular, this patent discloses a process for detecting "boar taint" in carcasses of non-castrated boars. According to the disclosed method, IR-spectrophotometrical transmission data is determined for the individual carcass or part and this spectral data is compared with corresponding data having a statistical relationship to boar taint.

While various methods have been disclosed in the prior art for determining microbial growth, such methods suffer from a number of drawbacks and are not generally and easily usable.

SUMMARY OF THE INVENTION

In accordance with the present invention, a quick simple and effective method for non-destructively determining genotypic and/or phenotypic characteristics of an unknown microbial organisms is provided which comprises the steps of:

inoculating a predetermined growth medium with an unknown microbial organism to create a microbial culture;

scanning the microbial culture with electromagnetic radiation at a time after inoculation to obtain a spectral signature, said scanning step conducted utilizing groups of contiguous wavelengths of electromagnetic radiation over a portion of the wavelength range from 700–5000 nm;

determining characterizing data of the unknown organism from the spectral signature;

comparing the characterizing data of the unknown organism with a preexisting library of characterizing data of known organisms with known characteristics, which library was made by scanning known organisms in the same manner as the unknown organism, to determine if there is a match between the characterizing data of the unknown organism and the characterizing data of a known organism contained in the library; and identifying the characteristic of the unknown organism when a match is found.

In this manner, characteristics such as identify, growth rate, and quantity of an unknown microbial organism can be rapidly and reliably detected in an efficient and reliable manner.

It is an advantage of the present invention that microbial growth can be measured quickly and easily with little or no human intervention.

It is also an advantage of the present invention that microbial growth can be measured in both a broth as well as solid agar plates.

It is a further advantage of the present invention that microbial growth is dynamically monitored in a culture medium without any destruction of the microbial organism.

Still another advantage of the present invention is that the effects of an antibiotic substance on microbial growth can be quickly and easily determined.

Other features and advantages of the present invention are as stated in or apparent from a detailed description of the presently preferred embodiments found hereinbelow.

DETAILED DESCRIPTION OF THE PREFERRED EMBODIMENTS

Figure 1:
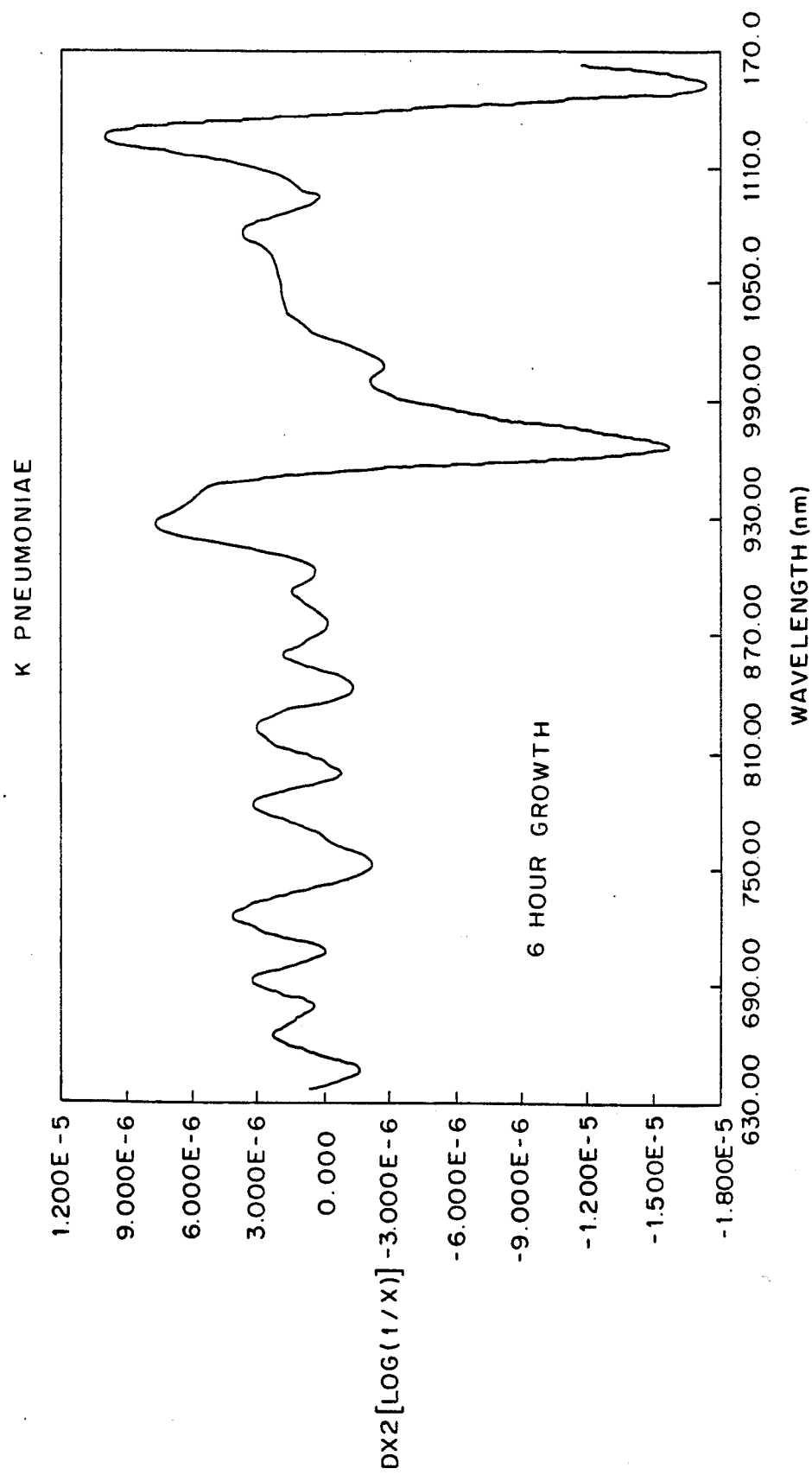
FIG. 1 is a graphical representation of the second derivative of the log of the inverse of the transmission at a particular wavelength versus wavelength of Klebsiella pneumoniae on Meuller-Hinton agar after 6 hours growth which has been processed (mathematically, to remove the effects of the medium) to show features of spectral signatures.

Spectroscopy is based on the fact that each atom or molecule has its own unique "signature" over the electromagnetic spectrum in terms of its spectral peaks or energy resonance frequencies. Spectroscopic signatures are dependent upon the characteristics of the substance under study as well as the excitation sources. Near-infrared/Mid-infrared (NIR/MIR) spectroscopy in particular, deals with excitation and spectral response of substances over the window of 700 to 5000 nm wavelength of the electromagnetic.

The concept of modern spectrometers is as follows:

1. A monochromatic (narrowband) radiation source is generated at a specified wavelength by a variety of means including fixed, tilting and rotating filters, rotating holographic diffraction gratings, infrared emitting diodes, and lasing diodes.
2. This radiation is directed at a sample (known) substance which has also been assayed by another well established methodology.
3. The reflected and/or transmitted signal is detected, measured and stored.
4. The signal data (spectrum) corresponding to the NIR/MIR range of radiation excitation wavelengths eventually becomes the signature for that particular substance.
5. Subsequently, statistical analysis routines are used to correlate the spectral data at particular wavelengths which characterize the sample substance with the assayed values from the well established methodology (the development of a learning curve).

6. Once these correlations are made, the presence of the characterizing data, such as absorption readings at particular wavelengths, can be used to determine the substance and its concentration in an unknown sample.

By the present invention, this general concept has been applied to microbial organisms. The unknown microbial organism can thus be characterized by a spectral signature which is the sum total of the organism and its interactions with its environment (culture medium and atmospheric conditions) at a particular temperature and point in time. A spectral signature in this regard is defined as an absorption pattern from a group of contiguous wavelengths to which a target substance is exposed, and characterizing data from the signature can include absorption readings from one or two characterizing wavelengths which have been found to determine the identity of an organism, its characteristics, quantity, and/or metabolic products. For most readings taken using scans of the present invention, it is generally the case that absorption data at one or two particular wavelengths is needed at a minimum to identify characteristics of a given organism.

The recorded spectral signature can represent changes in the cultured medium resulting from the increasing numbers of the microbial organism itself, the decreasing presence of certain nutrients in the medium (which nutrients have been altered by the growing organism), the presence of intermediate products produced by the organism, or the addition of defecation products to the medium. In any event, no matter what is exactly being measured, the spectral signature is a function of the microbial organism and can serve to determine its identity and growth. For example, in each spectral signature for a particular microorganism, there will be at least one determinable absorption reading from the data which will be correlated with the growth or quantity of the organism. This is specifically the case with the absorption line at about 1410 nm. It should also be appreciated that the medium can be seen as a convenient holder of the organism, and the medium is not necessary if the organism can be measured directly. Similarly, if the changes to the culture medium are what is being measured, the cells can be removed if desired.

The determination of the above parameters is typically made by comparing the characteristic data of the spectral signature of the unknown organism (either the full spectrum of wavelengths scanned or characterizing readings at specific wavelengths) with a spectral library of known characterizing data which have been correlated to values derived from standard laboratory tests. These standard tests can be used to determine normal growth rate, quantities at given times, or sensitivity to antibiotics of known microbial organisms in particular media at given temperatures.

Furthermore, if the identity of microorganism and its quantity can be determined at a specific point in time, its growth rate can then be determined by measuring the change in its quantity over unit time intervals.

In some cases, it is possible to identify a microbial organism, certain of its characteristics, or its quantity by an observation of absorption readings at particular characterizing wavelengths unique to a given organism which correlate to the desired characteristic sought to be determined. Under these circumstances meaningful measurements can be made independent of time after inoculation.

Since the microbial metabolic activities are a constant source of environmental change (as reflected in the culture medium), identical organisms having the same metabolic activities will change in the same ways over time. Thus, scanning at defined time intervals allows all samples to be compared from a common reference point and related to the library of known organisms referenced in the same way.

Figure 2:
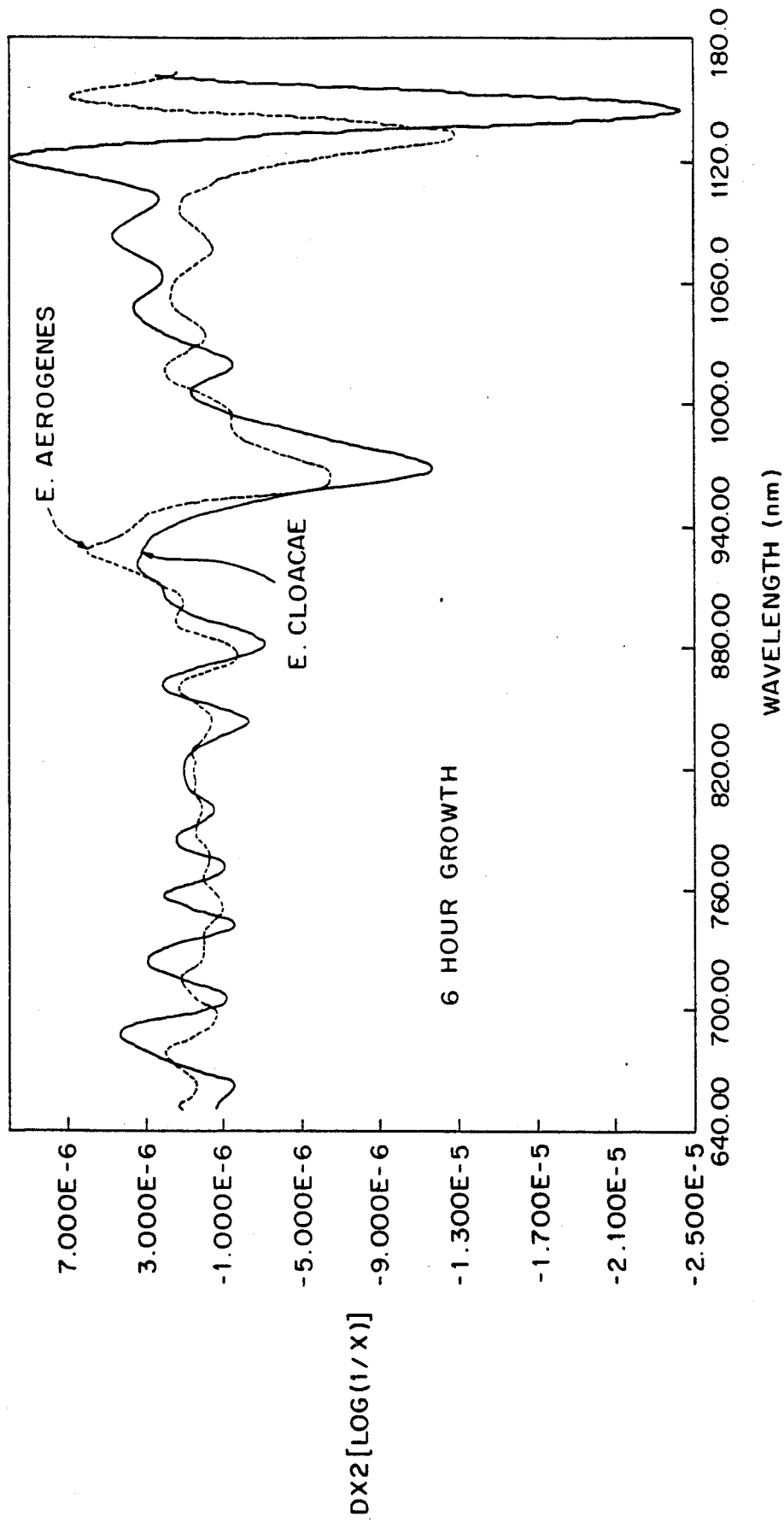
FIG. 2 is a graphical representation of the second derivative of the log of the inverse of the transmission at a particular wavelength versus wavelength of Enterobacter aerogenes and cloacae on Meuller-Hinton agar which compares different species of the same genus after 6 hours growth and which has been processed to show features of spectral signatures.
Figure 3:
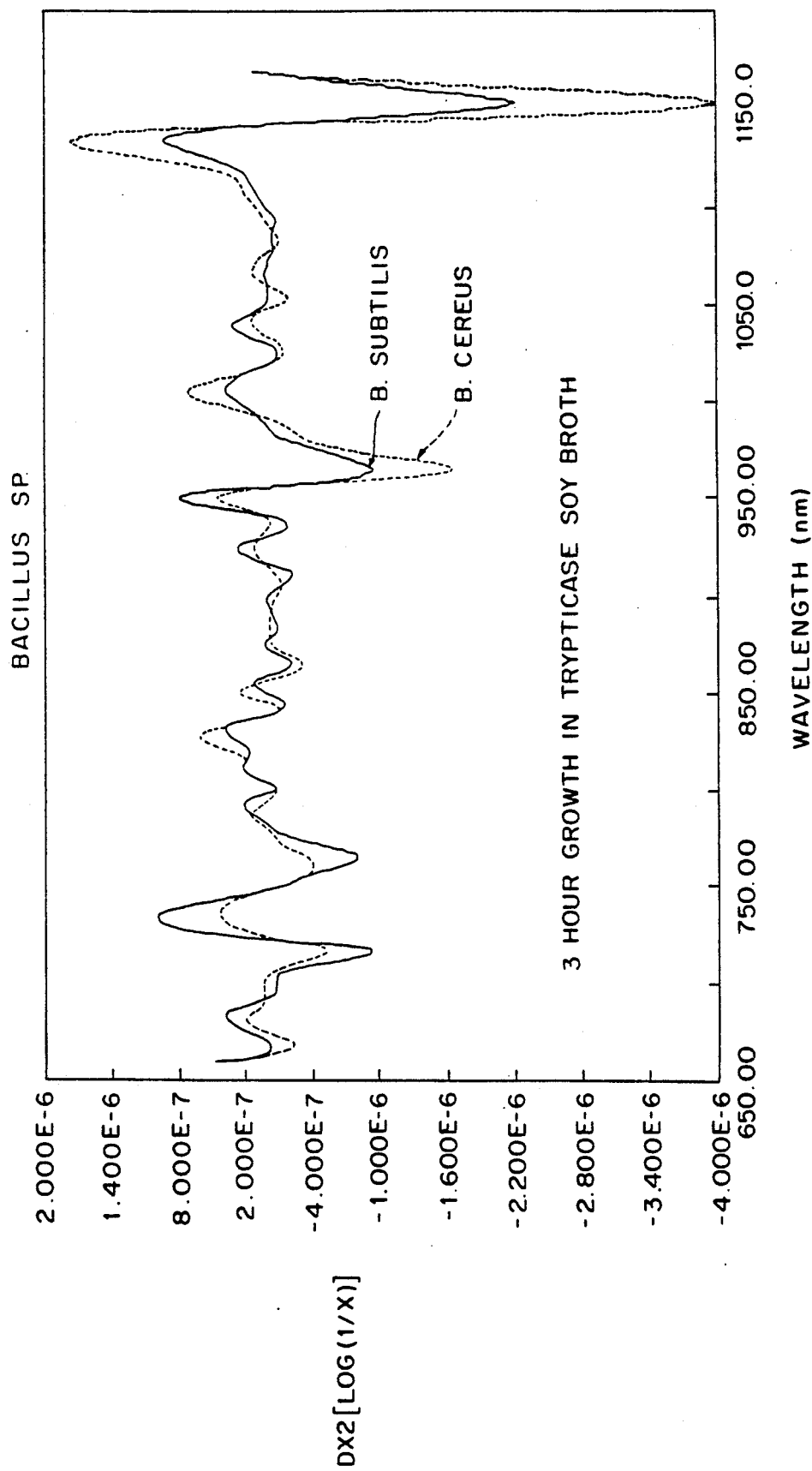
FIG. 3 is a graphical representation of the second derivative of the log of the inverse of the transmission at a particular wavelength versus wavelength of Bacillus cereus and substilis in trypicase soy broth which compares different but closely related species of the same genus after 3 hours growth and which has been processed to show features of spectral signatures.

Two types of measurements with respect to time are particularly useful. One is a single scan which acts as a snapshot at a particular instant, from which the identity of a microbial organism, its characteristics, and its quantity may be derived. FIGS. 1, 2, and 3 are examples of such spectral signatures. FIGS. 2 and 3 further show that the spectral signatures of even closely related species are different.

Figure 4:
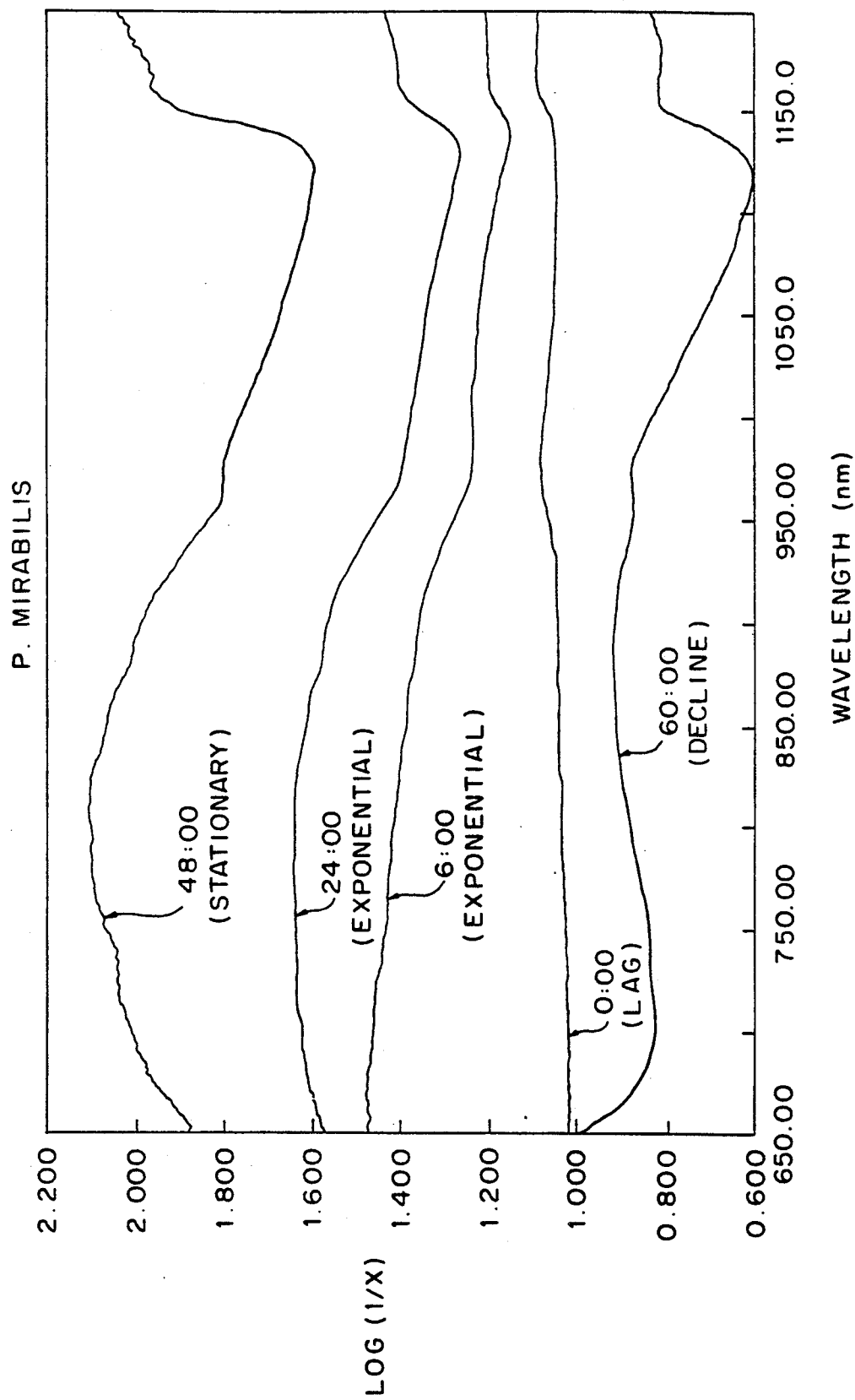
FIG. 4 is a graphical representation of the transmission (in arbitrary units) at a particular wavelength versus wavelength of Proteus mirabilis on Meuller-Hinton agar which shows all microbial growth phases at 0 to 60 hours and which is processed to show changes about the Y axis.

The second type of measurement with respect to time which is useful is a series of scans taken at unit time intervals. This allows the quantities of the organism to be compared, and thus the growth rate to be determined. An example of this is shown in FIG. 4 which shows the growth of an organism through the decline phases.

Time or series scanning can have two other functions in microbial organism classification. The spectral changes over time of each living organism are also unique. Thus they can be used as the basis for deriving the identity of a microbial organism and its characterizing features as well.

Figure 5:
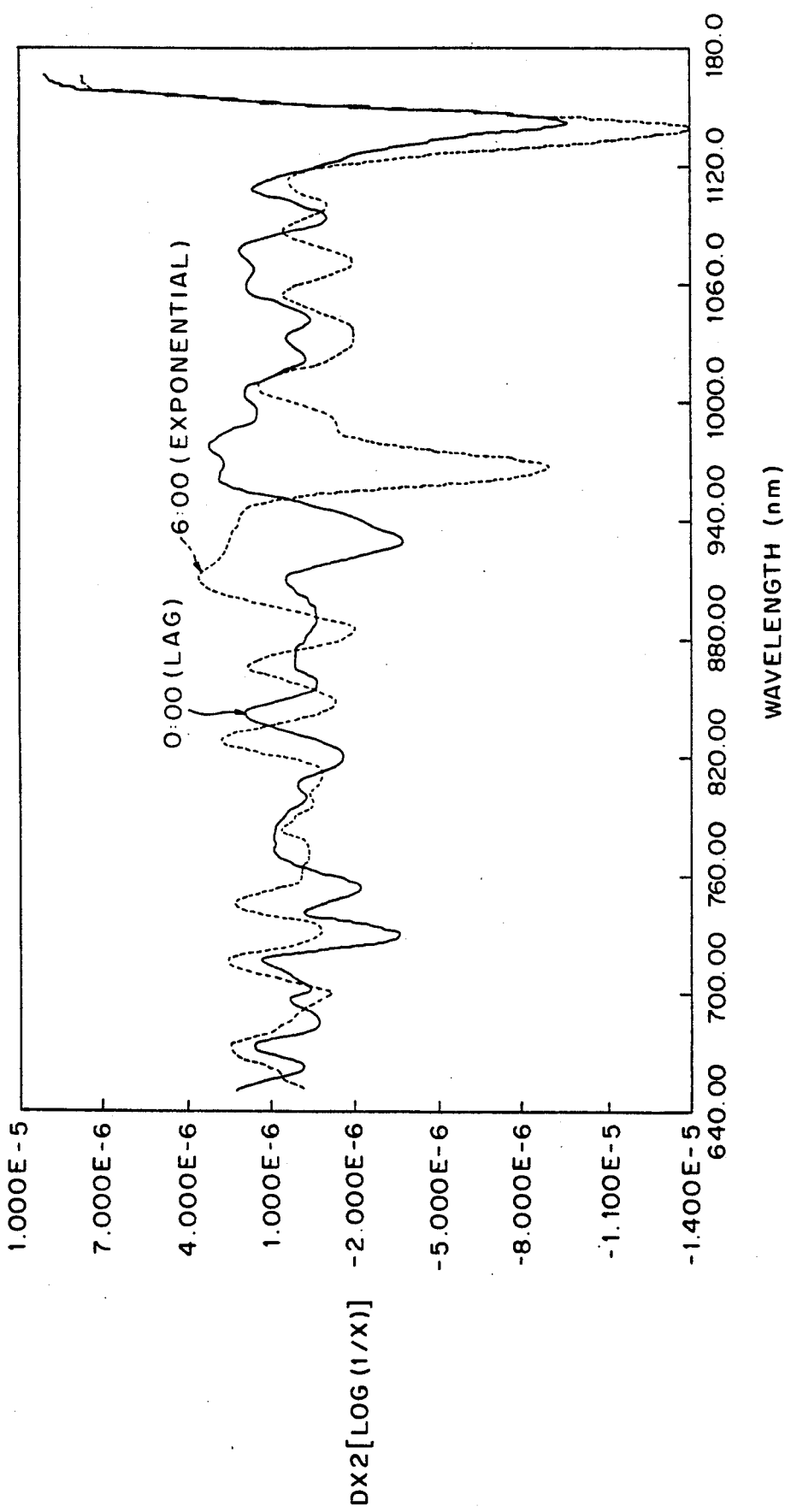
FIG. 5 is a graphical representation of the second derivative of the log of the inverse of the transmission at a particular wavelength versus wavelength of Proteus mirabilis on Meuller-Hinton agar which compares lag and exponential phases at 0 and 6 hours and which has been processed to show features of spectral signatures.

It should also be appreciated that after cells are inoculated in a growth medium there is an increase in macromolecular components and metabolic activity as the organisms prepare for cell synthesis. These changes associated with the lag phase can also be measured by taking serial scans beginning immediately after inoculation. This is also illustrated in FIG. 5.

Figure 6:
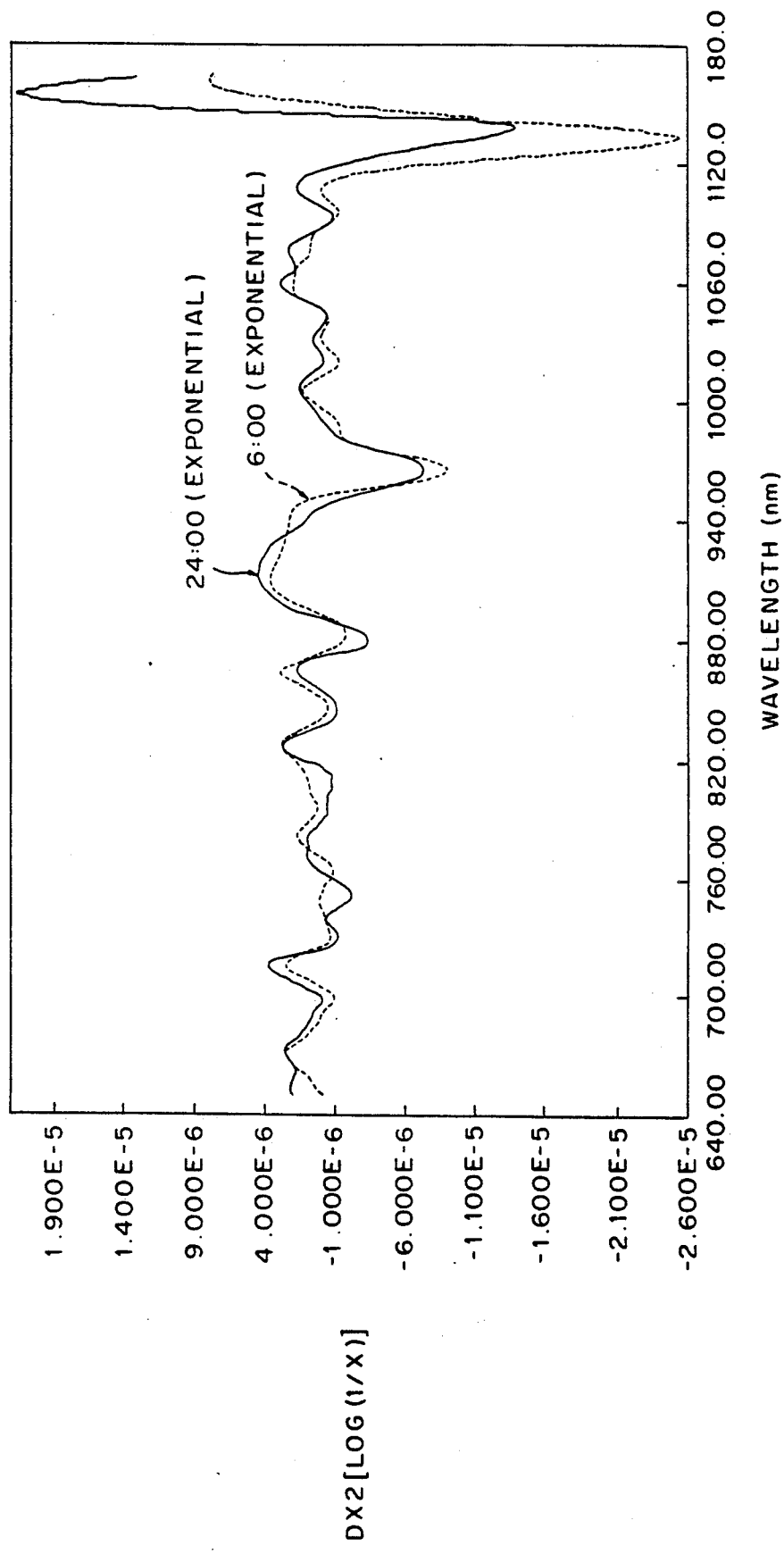
FIG. 6 is a graphical representation of the second derivative of the log of the inverse of the transmission at a particular wavelength versus wavelength of Proteus mirabilis on Meuller-Hinton agar which compares exponential phases at 6 and 24 hours and which has been processed to show features of spectral signatures.

During the exponential phase, the cells are in a balanced state of growth. In particular, the mass and volume of the cells increase in a manner such that the average composition of cells and relative concentrations of the metabolites remains constant. As cell multiplication proceeds, distinctive features and characteristics of the organism become more pronounced. This makes it possible to determine not just the identity of the organism, but other characteristics such as its sensitivity to particular antibiotics. Serial scans taken during this phase have relatively constant signatures as shown in FIG. 6. Such serial scans also show a distinct migration of the tracings along the Y axis which can be associated with an increase in cell numbers as shown in FIGS. 4 and 6.

Figure 7:
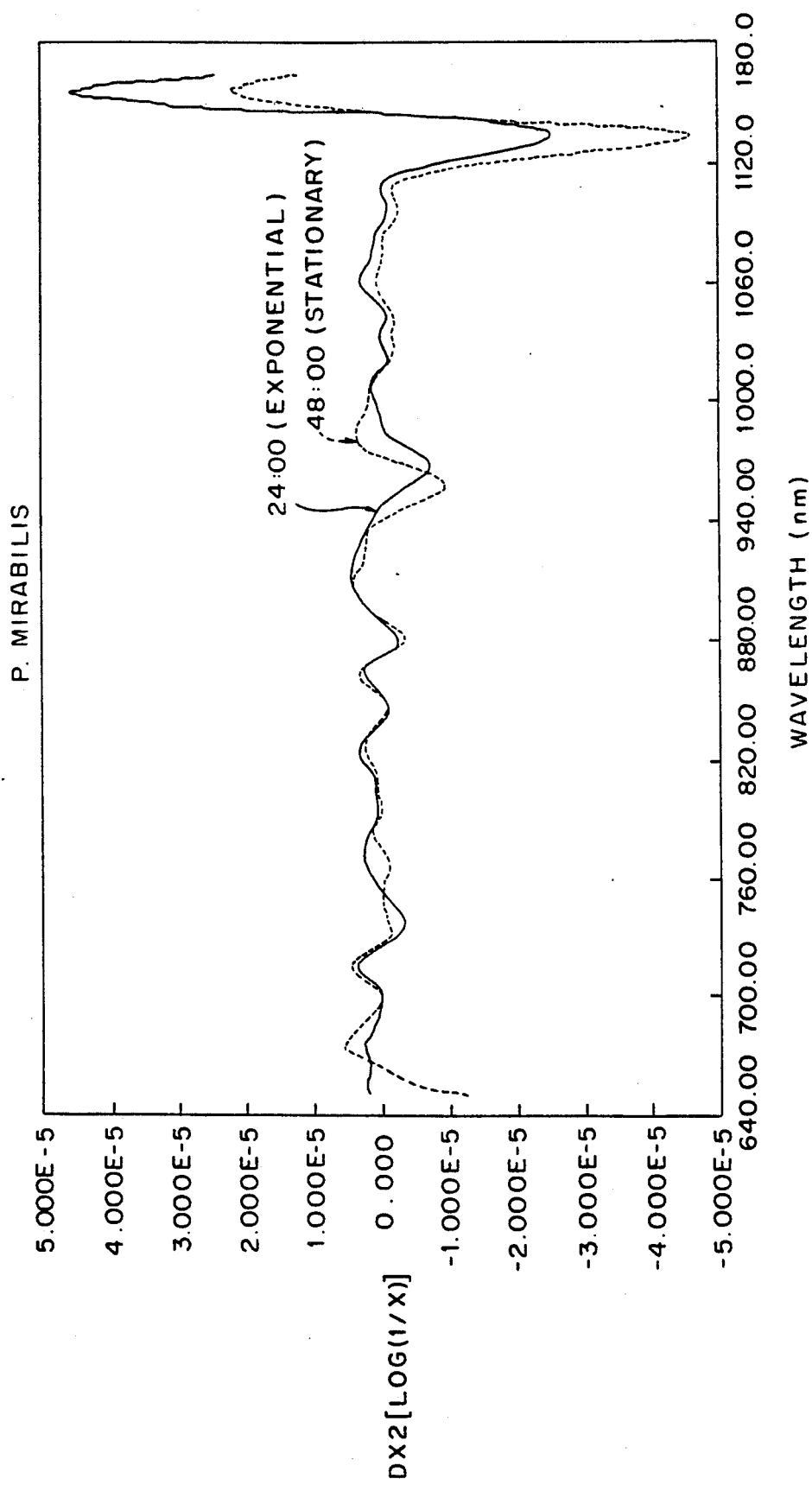
FIG. 7 is a graphical representation of the second derivative of the log of the inverse of the transmission at a particular wavelength versus wavelength of Proteus mirabilis on Meuller-Hinton agar which compares exponential and stationary phases at 24 and 48 hours and which has been processed to show features of spectral signatures.

In the stationary phase, the accumulation of waste products and exhaustion of nutrients result in a decreased growth rate with the maintenance of a constant cell count. Scans taken during this phase demonstrate some changes in spectral signatures as shown in FIGS. 4 and 7, and show no migration along the Y axis (see FIG. 4).

Figure 8:
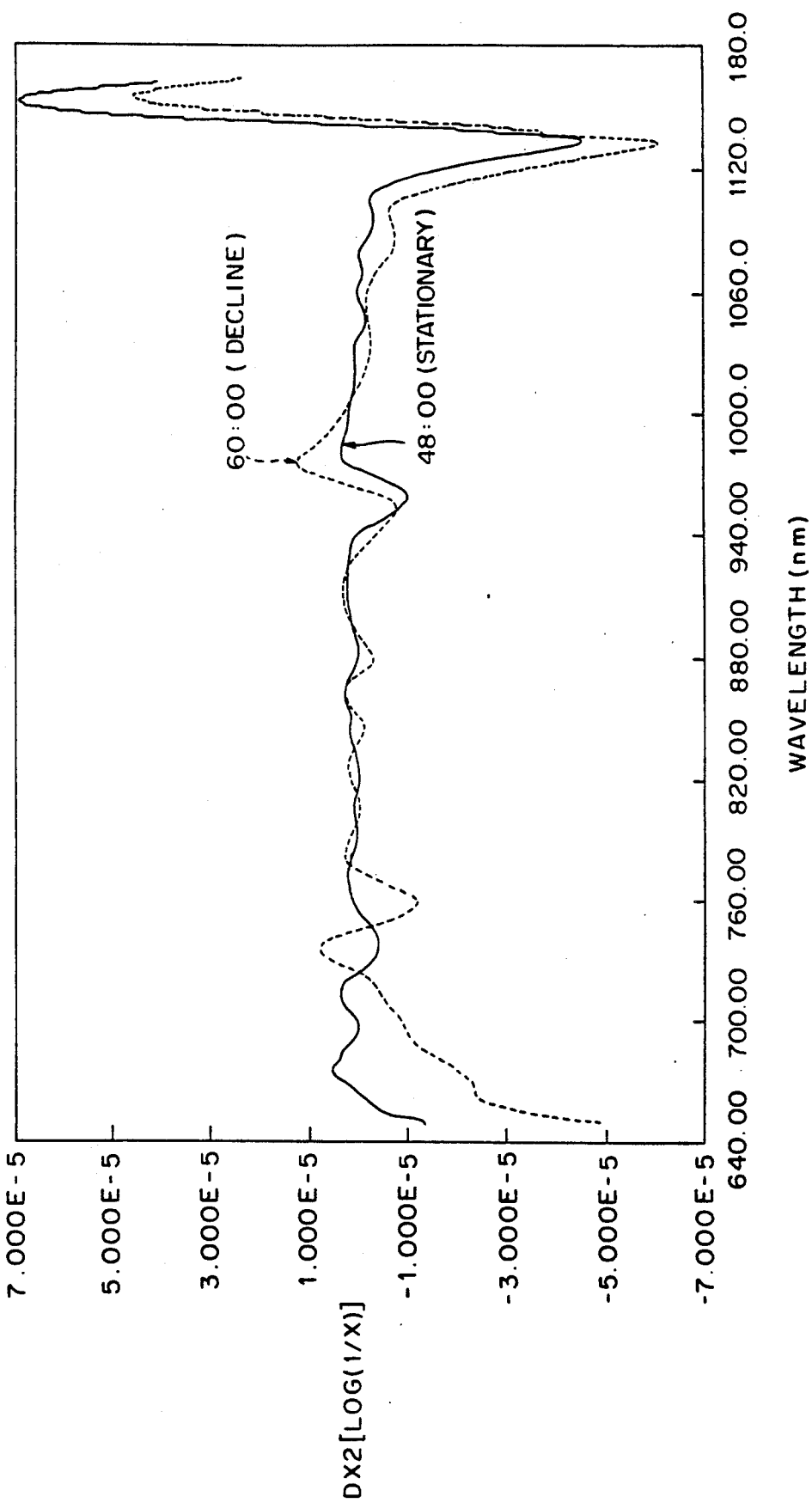
FIG. 8 is a graphical representation of the second derivative of the log of the inverse of the transmission at a particular wavelength versus wavelength of Proteus mirabilis on Meuller-Hinton agar which compares stationary and decline phases at 48 and 60 hours and which has been processed to show features of spectral signatures.

In the decline phase, the continual accumulation of waste products and exhaustion of nutrients result in deleterious effects on cell growth with a resulting decrease in numbers and changes in cell structure. These changes in cell structure result in cell degeneration, and this degeneration strongly affects overall absorption, as reflected in the recorded scans at this time. Scans taken during this phase reflect large changes in spectral signatures as shown in FIG. 8 and reverse migration of the spectral lines along the Y axis as shown in FIG. 4.

With the present invention, it should also be appreciated that measurements may be made in three different modes: transmission, reflectance, and transflectance. In transmission, the specimen is placed between the instrument's emitter and detector with the radiation passing through the sample. In reflectance, the specimen is oriented such that the incident radiation from the emitter is allowed to reflect from the surface and subsurface of the specimen into the detector. When this mode is utilized a fiber optic extension can be a useful adjunct. In transflectance, the specimen is oriented so that the radiation from the emitter is allowed to reflect off a surface below the specimen such that it passes completely through the sample in both its incident path into the specimen and reflected path leaving the specimen for the detector.

In all the modes of measurement, it is preferable to use procedures adapted to the type of growth medium employed. In the case where solid growth medium such as agar is utilized, it is desirable to prepare the sample by covering the surface of the medium with a suspension of the microbial organism in question. Then, the excess is drawn off, in order to achieve an even distribution. During the reading of the specimen, it is also useful to employ a rotating platform upon which the sample is mounted. This allows for any uneven surface distributions of microbial organisms to be averaged and thus readings from local accumulations or deficiencies would cause less overall distortion in spectral signatures.

In the case where a liquid growth medium such as trypticase soy broth is used, means must be employed to prevent clumping and settling of the microbial organisms in suspension. Such means include agitation, filtration, air jets, the use of flow cells, and the addition of detergents. Different media, whether solid or liquid, can be employed based on the suspected type of unknown organism scanned, and it will be clear to one skilled in this art that a number of suitable media can be used in the invention, but that specific types of media will be favored in given situation.

The specimen preparation is a two step procedure which involves taking an initial scan of the growth medium by itself and then inoculating the medium with the microbial organism in question. The spectral signature of the initial scan is saved in computer memory to be used later as a background reference.

During data acquisition, the moment of inoculation is used as the zero time, or starting point against which all subsequent scans are referenced. In the preferred method, the initial scan is used as a background by dividing or subtracting it out from any subsequent scans made after inoculation with a microbial organism. This is advantageous to more easily view any subsequent changes. However, other methods besides dividing out the background medium have proved useful, such as dividing by water as a background.

In certain cases, the identification of microbial organisms can be enhanced by specimen processing. This includes harvesting of the culture medium separated from the cells, or the isolated cells themselves for scanning after a suitable incubation period. Thus, either the whole culture can be scanned (which is typically the case) or some portion of the whole culture (the medium or cells) can be scanned.

Enhanced processing also includes adding substances to the medium which can be utilized by microbial organisms and which also have strong definitive spectral characteristics. Thus, as these substances are metabolized by bacteria, they provide spectral markers, changing at rates which are specific to the metabolism of the organism in question. Such substances include amino acids, fatty acids, NIR absorbing dyes, and the like which can be tagged to specific metabolites utilized by microbial organisms.

It should also be appreciated that in the NIR region of the spectrum, water absorption blankets much of the signal produced by substances in solution. Thus, by eliminating the water, the sensitivity of the measurements is greatly increased. As a consequence, detection of the characteristics of microbial organisms and their growth rates are made at an earlier time. One technique for eliminating water is rapidly drying the sample. By incorporating such a technique into the overall procedure, this decreases the time for identifying positive results and extracts more information from the data than would otherwise be possible.

It is also possible to directly scan a specimen taken from a patient. Where the specimen contains a number of organisms, the identification of one or all of the organisms may be somewhat complicated. However, where it is desired to determine the presence or absence of only a single specific organism, such a determination can be easily made. For example, such infections as urinary tract infections and CSF (cerebral spinal fluid) almost always are caused by only a single respective organism. Thus, a specimen suspected of containing a specific infectious organism can be immediately scanned for that organism. Based on this scan, the presence (or absence) of the specific organism in the specimen is determined by looking for the relevant (predetermined) characterizing data. The identification of one or more organisms directly from a specimen can also be enhanced by drying the specimen, as discussed above.

The scans are taken utilizing a sample compartment which is designed to keep out interfering radiation, and maintain a constant temperature.

Testing for sensitivity of a microbial organism to a series of different antibiotics can be accomplished by three methods or by utilizing them in any combination.

One methodology is the detection of growth cessation in the presence of an antibiotic. This methodology measures growth rates in a series of culture media each infused with a different antibiotic. A suspension containing the microorganism in question is introduced into each of the series of culture media. Then sequential spectral signatures are taken at unit time intervals and characterizing data from the spectral signatures are compared with previous ones until the changes associated with growth cease. The sensitivity of the organism to the antibiotic is determined by its ability to cause cessation of growth over time.

Figure 9:
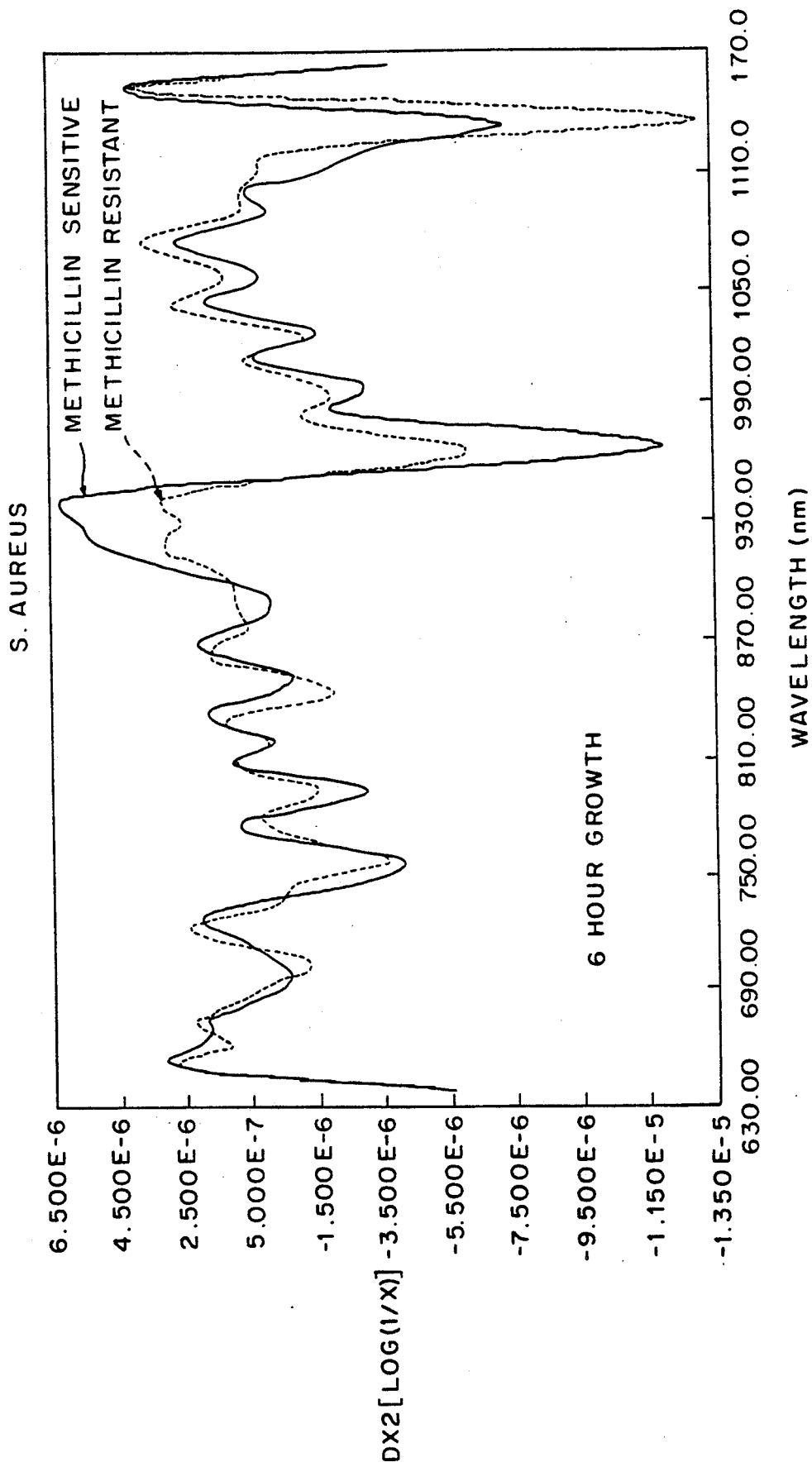
FIG. 9 is a graphical representation of the second derivative of the log of the inverse of the transmission at a particular wavelength versus wavelength of Staphylococcus aureus and Meuller-Hinton agar which compares Methicillin sensitive and resistant strains at 6 hours and which has been processed to show features of spectral signatures.

A second methodology is the detection of antibiotic sensitivity or resistance directly from the spectral signatures in the absence of an antibiotic. Beginning with a pure culture grown in a medium without antibiotic additives, the characterizing data from the spectral signature has information which can be related to the antibiotic sensitivity or resistance of an organism. For example, as shown in FIG. 9, methicillin sensitive and resistant strains of the same organism have different spectral signatures.

A third methodology is the detection of antibiotic sensitivity or resistance directly from the spectral signatures in the presence of an antibiotic. Microbial organisms exhibit a unique spectral signature for each specific medium in which they are grown. They also exhibit a unique signature for each antibiotic media mixture to which they are exposed. Therefore, it is possible to rapidly identify a pure microbial strain from its signature when grown in a medium with an antibiotic additive, as well as determine its sensitivity or resistance. Examples of this are shown in FIGS. 10-15.

Figure 10:
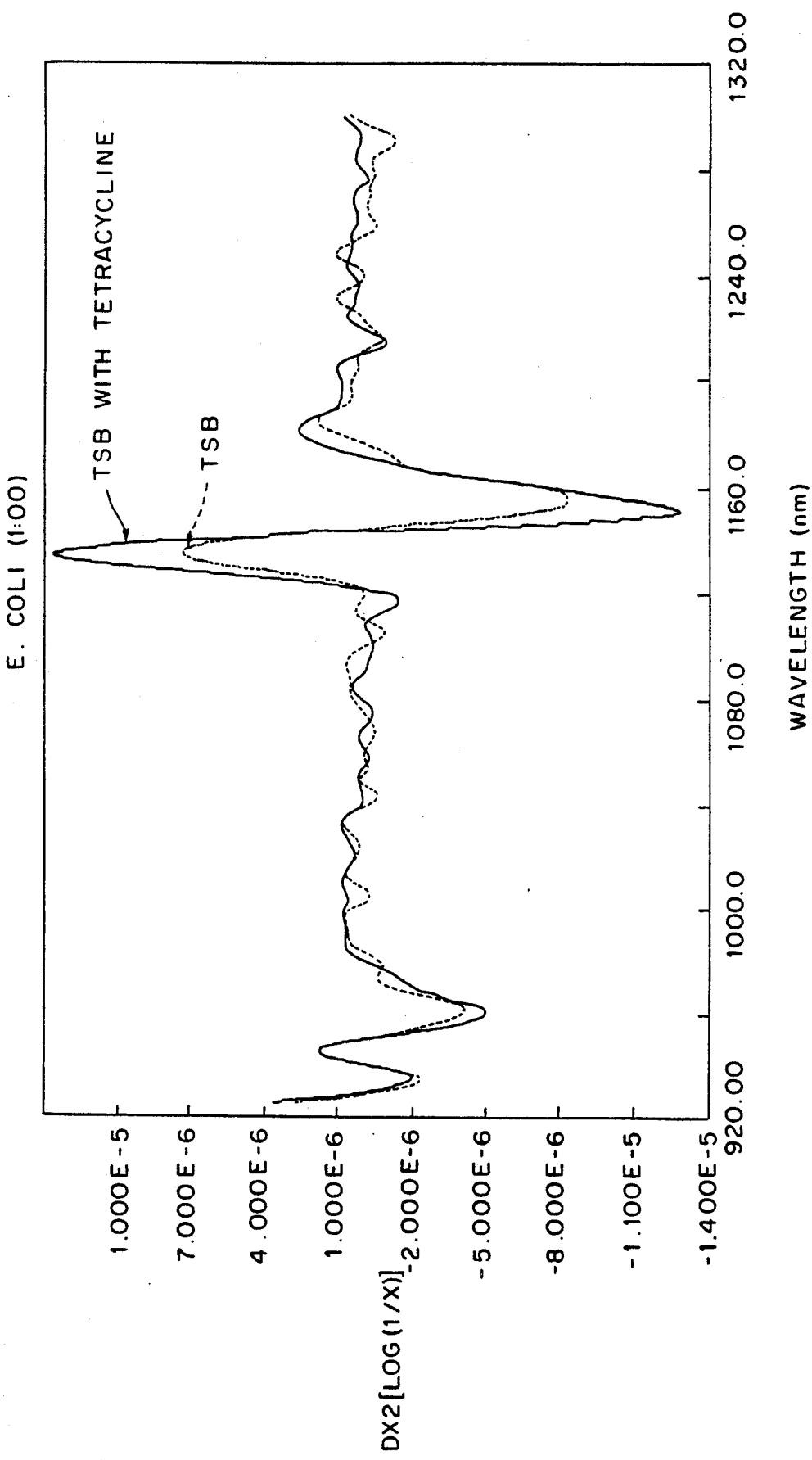
FIG. 10 is a graphical representation of the second derivative of the log of the inverse of the transmission at a particular wavelength versus wavelength which compares Escherichia coli in trypicase soy broth alone and with tetracycline additive after 1 hour growth and which has been processed to show features of spectral signatures.
Figure 11:
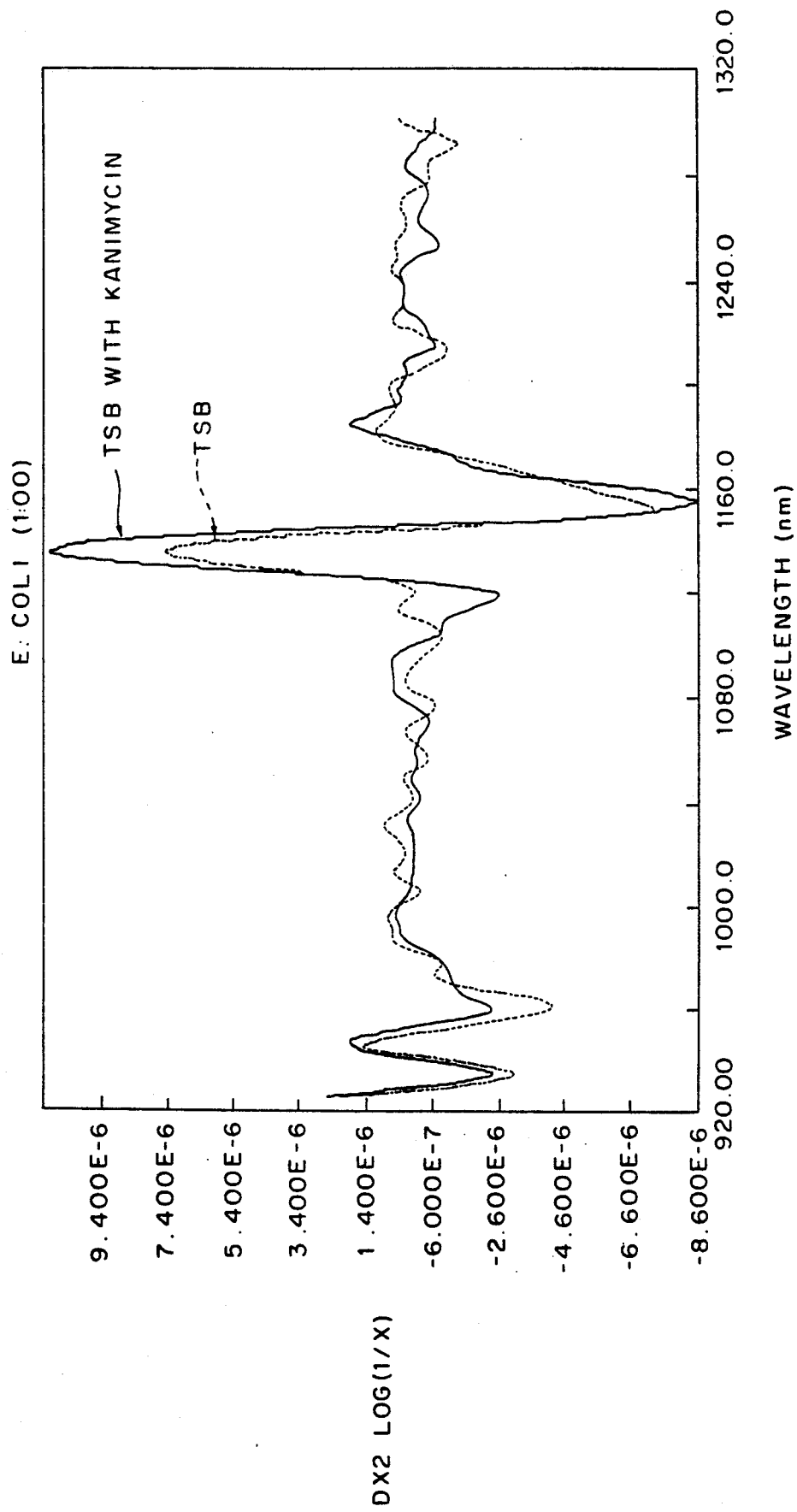
FIG. 11 is a graphical representation of the second derivative of the log of the inverse of the transmission at a particular wavelength versus wavelength which compares Escherichia coli in trypticase soy broth alone and with kanamycin additive after 1 hour growth and which has been processed to show features of spectral signatures.
Figure 12:
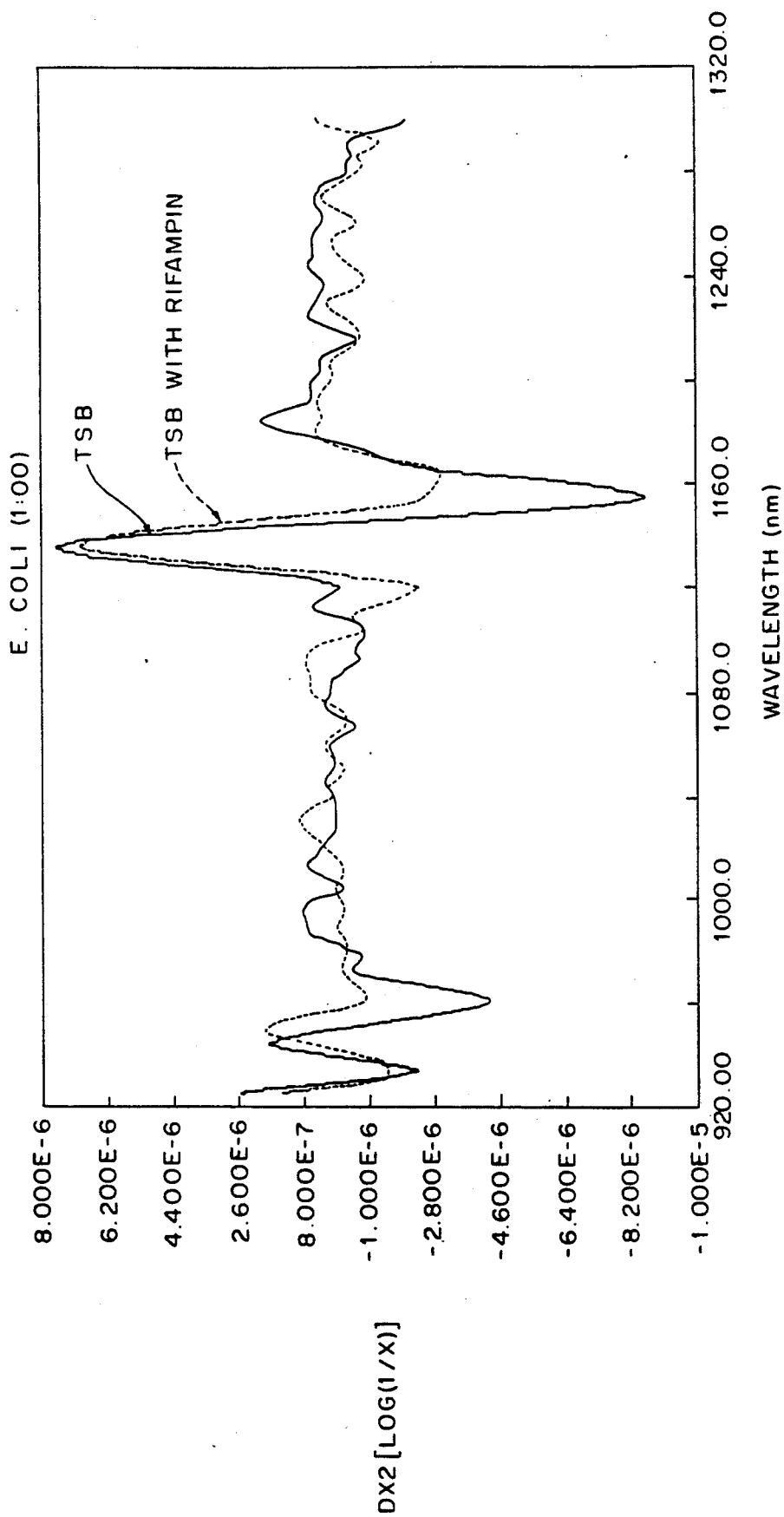
FIG. 12 is a graphical representation of the second derivative of the log of the inverse of the transmission at a particular wavelength versus wavelength which compares Escherichia coli in trypticase soy broth alone and with rifampin additive after 1 hour growth and which has been processed to show features of spectral signatures.
Figure 13:
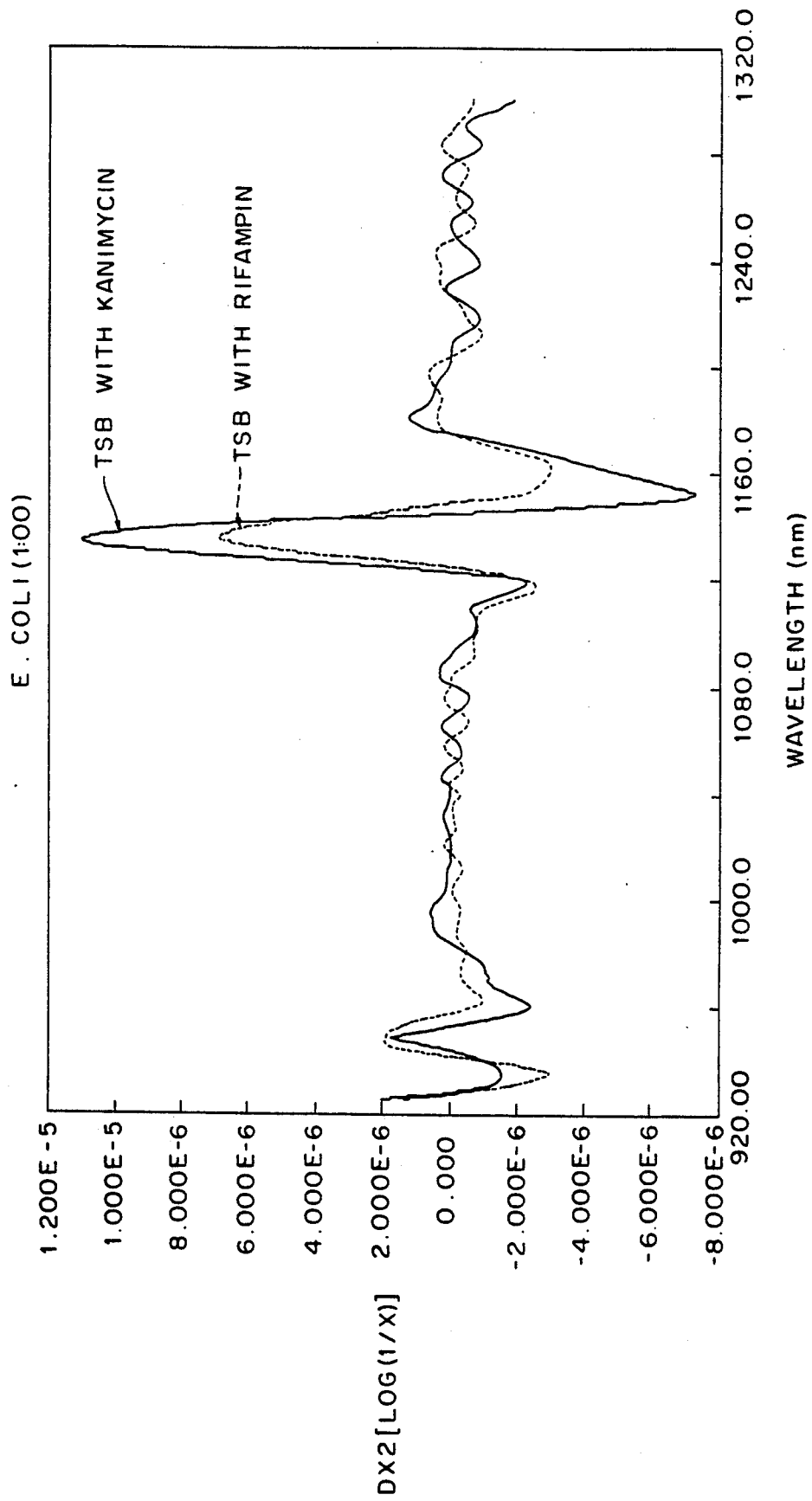
FIG. 13 is a graphical representation of the second derivative of the log of the inverse of the transmission at a particular wavelength versus wavelength which compares Escherichia coli in trypticase soy broth alone and with kanamycin and rifampin additive after 1 hour growth and which has been processed to show features of spectral signatures.
Figure 14:
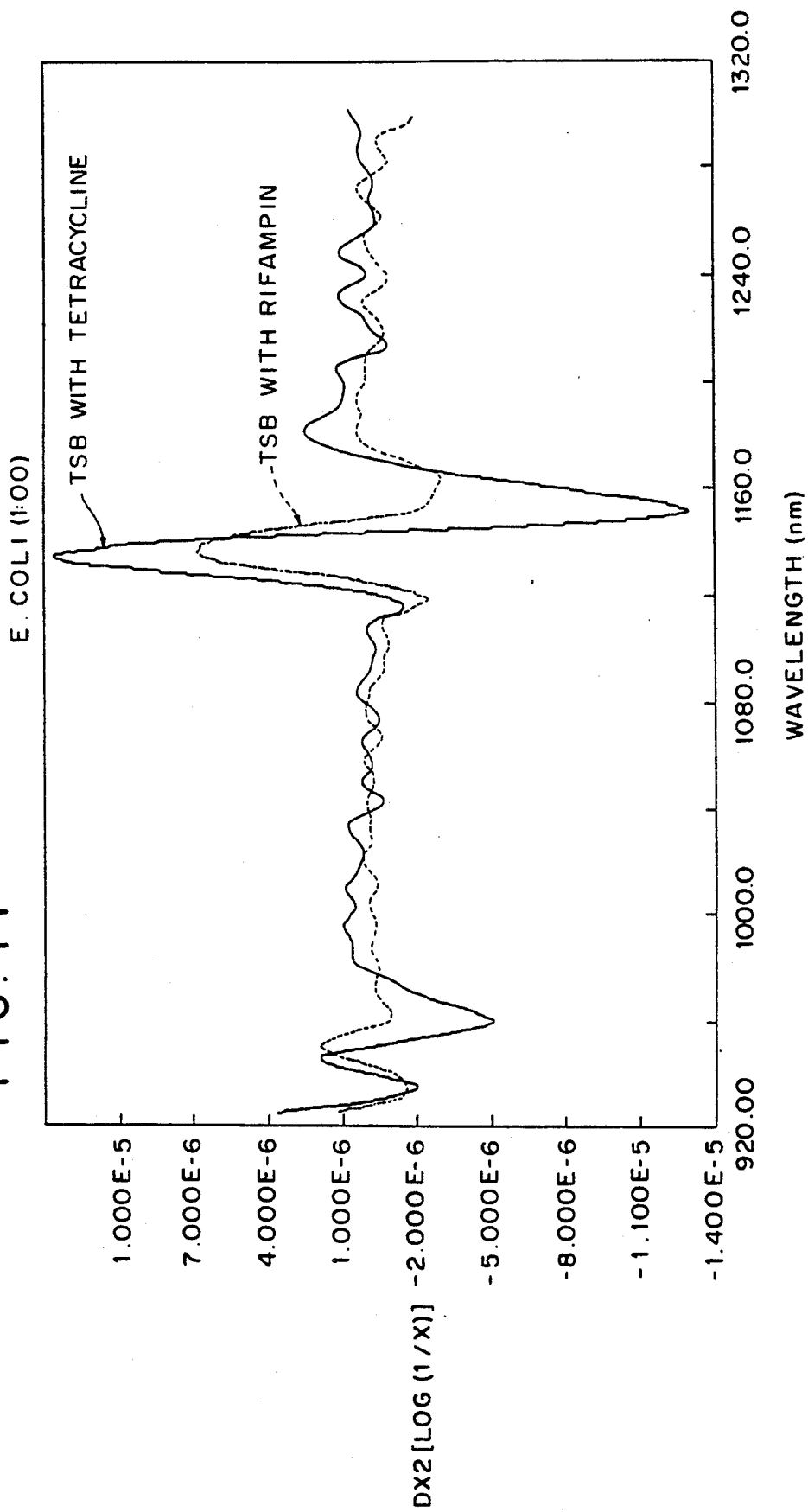
FIG. 14 is a graphical representation of the second derivative of the log of the inverse of the transmission at a particular wavelength versus wavelength which compares Escherichia coli in trypticase soy broth alone and with tetracycline and rifampin additive after 1 hour growth and which has been processed to show features of spectral signatures.

In the first and third methods for the detection of antibiotic sensitivities, it is useful to run a control consisting of media without an antibiotic additive as shown in FIGS. 10-12. This can be used to compare the organism in question with a library of known characterizing data from previously recorded spectral signatures for an additional identity check, as well as to serve as a comparative for the organism grown with the antibiotic additives.

Figure 15:
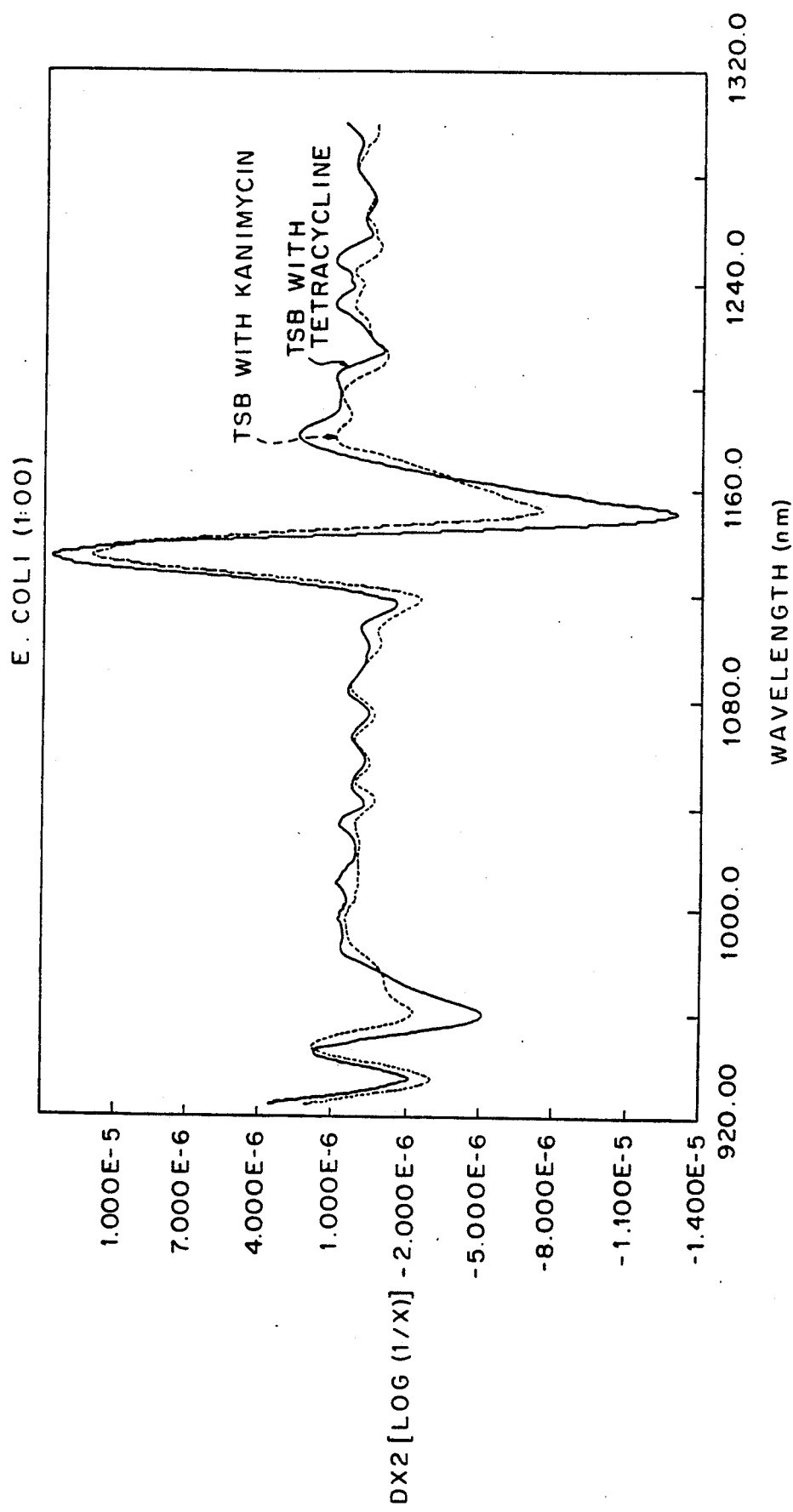
FIG. 15 is a graphical representation of the second derivative of the log of the inverse of the transmission at a particular wavelength versus wavelength which compares Escherichia coli in trypticase soy broth alone and with tetracycline and rifampin additive after 1 hour growth and which has been processed to show features of spectral signatures.

It should also be noted that the tracings of the effects of two different antibiotics on the same organism in FIG. 15 are very similar. This is because both antibiotics have the same mechanism of action (they inhibit protein synthesis at the level of the 30S ribosomal subunit) eve though both antibiotics have different chemical structures.

Currently with the method employed by the prior art, an antibiotic sensitivity test takes twenty-four hours after isolation of the organism in question. One reason for this is that the identity of the organism is not known and therefore this time period must account for all organisms, including the slow growing, which take longer for the results of their growth in the presence of an antibiotic to show up. Another reason is that traditionally the identity and antibiotic sensitivity of a microbial organism are reported to the physician together, and the identity is run concurrently with the antibiotic sensitivity and also takes twenty-four hours.

Utilizing scanning spectroscopy, according to the present invention, the identity of an organism can be made simultaneously with the antibiotic sensitivity screening all on the same specimen with the same instrument. Thus it becomes possible to report results as they become available. For fast growing organisms, such as Escherichia coli, this can be far less than twenty-four hours.

The other major advantage of the described methodology is the saving realized in labor. Once a specimen is set up for finding its identity and antibiotic sensitivities (an easier procedure than currently used), it can be read and reported out automatically by the computer interfaced to an instrument.

While there are a variety of ways to measure spectral signatures for a microbial culture, the "Quantum 1200 Analyzer" produced by LT Industries, Inc. of Rockville, Maryland has been found to be a particularly useful apparatus for this purpose. With this apparatus, the transmittance, reflectance, or transflectance of a sample in the near infrared through visible spectral range is easily determined. In transflectance, a ceramic dish is located behind the sample to reflect the incident radiation back through the specimen and to the detector. With the data produced by such a device, microbial growth can be quantitatively analyzed according to the present invention. It will be clear to one skilled in the art that any of various conventional scanning IR devices, will be suitable for taking the spectrophotometrical readings in the IR range in accordance with the present invention.

Obviously, it is preferred to use the same measuring instrument for each measurement of a sample. However, if necessary, different instruments could be used so long as a suitable calibration is made between the instruments.

While the present invention has been described with respect to exemplary embodiments thereof, it will be understood by those of ordinary skill in the art that variations and modifications can be effected within the scope and spirit of the invention.

I claim:

1. A method for determining the identity of an unknown microbial organism in a sample without destroying the microbial organism, comprising the steps of:
    (a) inoculating a growth medium with a sample containing a pure culture of an unknown microbial organism, said medium being capable of supporting the growth of said microbial organism, to create a microbial culture;
    (b) incubating said culture for a period of up to and including at least the exponential growth phase of said culture;
    (c) scanning the microbial culture, at a predetermined time point after inoculation, with electromagnetic radiation having a wavelength between about 700 and about 500 nm, and obtaining a spectral signature at a predetermined range of wavelengths therebetween so as to provide characterizing data of the organism; and
    (d) comparing visually or with the assistance of a computer said spectral signature obtained in step (c) with spectral signatures in a preexisting library of known characterizing data of known microbial organisms to determine if there is a match, said match indicating identity of the microbial organism, wherein said library of spectral signatures has been obtained by scanning the known microbial organisms under the same culture conditions and scan time points as in steps (a)-(c) above, thereby determining the identity of said microbial organism.

2. A method according to claim 1 wherein the spectral signature obtained in step (c) includes the entire wavelength range.

3. A method according to claim 1, wherein said scanning time point is in the exponential phase of growth of the unknown microbial organism.

4. A method according to claim 1, further comprising storing the spectral signature obtained in step (c) in computer memory where said library spectral signatures are also stored, and wherein said comparing step (d) is performed by accessing the computer memory.

5. A method according to claim 1, further comprising in step (c):
    scanning said microbial culture at a second time point after said first time point to obtain a second spectral signature, said second spectral signature being at a predetermined range of wavelengths, so as to provide additional characterizing data of the organism; and
wherein step (d) additionally comprises comparing said second spectral signature to said library of known spectral signatures.

6. A method according to claim 5, further comprising the step of:

(e) determining the rate of change of the characterizing data obtained as said first and said second spectral signatures wherein step (d) additionally comprises comparing said rate of change to said library of known spectral signatures, which library includes spectral signatures and rates of change of spectral signatures as characterizing data for said known organisms.

7. A method according to claim 6, further comprising storing the spectral signatures obtained in step (c) in computer memory where said library spectral signatures and rates of change are also stored, and wherein said comparing step (d) and said determining step (e) are performed by accessing the computer memory.

8. A method according to claim 5, wherein said first and said second time points are in the exponential phase of growth of the unknown microbial organism.

9. A method according to claim 1, further comprising, in step (c):

scanning said microbial culture at additional time points after said first time point to obtain an additional spectral signature, said additional spectral signature comprising additional characterizing data of the unknown organism;

and further comprising the step of:

(e) determining the rate of change of the characterizing data obtained as said first and said additional spectral signatures, wherein step (d) additionally comprises comparing said additional spectral signatures and said rates of change to said library of known spectral signatures, said library including spectral signatures and rates of change of characterizing data for known organisms.

10. A method according to claim 9, further comprising storing the spectral signatures obtained in step (c) and said rates of change determined in step (d) in computer memory where said library spectral signatures and rates of change are also stored, and wherein said comparing step (d) and said determining step (e) are performed by accessing the computer memory.

11. A method according to claim 9, wherein said first and said additional time points are in the exponential phase of growth of the unknown microbial organism.

12. A method according to claim 1, wherein said microbial organism is a bacterium.

13. A method according to claim 12, wherein said bacterium is a gram positive or a gram negative bacterium.

14. A method according to claim 1, additionally comprising adding to said culture medium a substance having at least one strong definitive spectral characteristic when it has been in contact with, and has been transformed by, said organism, such that when said substance has been transformed, a characterizing change in the spectral signature is obtained.

15. A method according to claim 14, wherein said added substance is selected from the group consisting of amino acids, fatty acids and near-infrared absorbing dyes.

16. A method according to claim 1, further comprising the step of eliminating water from the microbial culture before said scanning step (b) and scanning the microbial culture from which the water has been eliminated.

17. A method according to claim 1, further comprising scanning a sample of the growth medium having no microbial organisms inoculated thereinto to obtain a base spectral signature, and mathematically removing the base spectral signature from the spectral signature obtained in step (c).

18. A method for determining antibiotic sensitivity of a microbial organism, comprising the steps of: destroying the microbial organism in a sample without (a) inoculating a control growth medium capable of supporting the growth of said microbial organism with a sample containing a pure culture of the microbial organism to create a control microbial culture;

(b) inoculating a test growth medium, said test medium being the same as said control growth medium but including an antibiotic, with a sample containing a pure culture of the microbial organism to create a test microbial culture;

(c) incubating said cultures for a period of up to and including at least the exponential growth phase of said cultures;

(d) scanning each of said cultures, at a predetermined time point after inoculation with electromagnetic radiation having a wavelength between about 700 and about 5000 nm, and obtaining a spectral signature at a predetermined range of wavelengths therebetween so as to provide characterizing data for the quantity of the organism in the cultures; and (e) comparing visually or with the assistance of the computer the spectral signatures of each said cultures to determine the quantity of the organism in said control and said test cultures, wherein a smaller quantity of the organism in said test culture is indicative of antibiotic sensitivity, thereby determining the antibiotic sensitivity of said microbial organism of said sample.

19. A method according to claim 18 wherein said scanning time point is in the exponential phase of growth of said microbial organism.

20. A method according to claim 18, wherein step (d) comprises scanning said cultures at two or more time points, resulting in two or more spectral signatures for each of said cultures, and wherein step (e) additionally comprises comparing the rate of change of the quantity of the organisms in each of said cultures over time.

21. A method according to claim 20, wherein said two or more time points are in the exponential phase of growth of said microbial organism.

22. A method according to claim 20, wherein said microbial organism is a bacterium.

23. A method according to claim 22, wherein said bacterium is a gram positive or a gram negative bacterium.

24. A method for determining the identity of an unknown microbial organism in a sample containing only one type of microbial organism, without destroying the microbial organism, comprising the steps of:

(a) obtaining said sample;

(b) scanning the sample with electromagnetic radiation having a wavelength between about 700 and about 5000 nm, and obtaining a spectral signature at a predetermined range of wavelengths therebetween so as to provide characterizing data of the organism; and (c) comparing visually or with the aid of a computer said spectral signature obtained in step (b) with spectral signatures in a preexisting library of known characterizing data of known organisms to determine if there is a match, wherein said library of spectral signatures has been obtained by scanning the known organisms in a similar type of sample as the sample of step (a),
thereby determining the identity of said unknown organism when a match is found.

25. A method according to claim 24, wherein said sample is urine or cerebrospinal fluid.

26. A method according to claim 24, further comprising a step of eliminating water from the sample before said scanning step (b) and scanning the sample from which the water has been removed.

27. A method according to claim 24, additionally comprising adding to said sample a substance having at least one strong definitive spectral characteristic when it has been in contact with, and has been transformed by, said organism, such that when said substance has been transformed, a characterizing change in the spectral signature is obtained.

28. A method according to claim 27, wherein said added substance is selected from the group consisting of amino acids, fatty acids and near-infrared absorbing dyes.

29. A method for determining the identity of an unknown microbial organism in a sample without destroying the microbial organism, comprising the steps of:
(a) inoculating a growth medium with a sample containing a pure culture of an unknown microbial organism, said medium being capable of supporting the growth of said microbial organism, to create a microbial culture;
(b) incubating said culture for a period of up to and including at least the exponential growth phase of said culture;
(c) at a predetermined time point after inoculation, removing any microbial organism cells from the growth medium, and separately scanning
   i. the growth medium lacking the cells,
   ii. the removed cells, or
   iii. both the growth medium lacking the cells and the removed cells,
with electromagnetic radiation having a wavelength between about 700 and about 5000 nm, and obtaining a spectral signature at a predetermined range of wavelengths therebetween so as to provide characterizing data of the organism; and
(d) comparing visually or with the assistance of a computer said spectral signature obtained in step (c) with spectral signatures in a preexisting library of known characterizing data of known microbial organisms to determine if there is a match, said match indicating identity of the microbial organism,
wherein said library of spectral signatures has been obtained by scanning growth medium lacking cells, removed cells, or both, obtained after a known microbial organisms has been cultured under the same culture conditions and scan time points as in steps (a)–(c) above, thereby determining the identity of said microbial organism.

* * * * *